United States Patent [19]

Sessler et al.

[11] Patent Number: 5,543,514
[45] Date of Patent: Aug. 6, 1996

[54] WATER-SOLUBLE SAPPHYRINS

[75] Inventors: Jonathan L. Sessler; Vladimir Král, both of Austin, Tex.

[73] Assignee: Board of Regents, The University of Texas System, Austin, Tex.

[21] Appl. No.: 417,940

[22] Filed: Apr. 6, 1995

Related U.S. Application Data

[63] Continuation-in-part of Ser. No. 964,607, Oct. 21, 1992, Pat. No. 5,457,195, which is a continuation-in-part of Ser. No. 454,298, Dec. 21, 1989, Pat. No. 5,159,065.

[51] Int. Cl.$^6$ .......................... C07D 487/22; C07H 9/00
[52] U.S. Cl. ...................... 540/472; 540/145; 536/123.1; 536/20; 536/3; 536/112
[58] Field of Search .................................. 540/472, 145; 536/123.1, 20, 3, 112

[56] References Cited

U.S. PATENT DOCUMENTS

| 4,318,825 | 3/1982 | Frame | 252/428 |
|---|---|---|---|
| 4,835,263 | 5/1989 | Nguyen et al. | 536/27 |
| 4,878,891 | 11/1989 | Millard | 604/5 |
| 4,883,790 | 11/1989 | Levy et al. | 540/145 |
| 4,915,683 | 4/1990 | Sieber | 604/4 |
| 4,935,498 | 6/1990 | Sessler et al. | 540/472 |
| 5,041,078 | 8/1991 | Matthews et al. | 674/4 |
| 5,120,411 | 6/1992 | Sessler et al. | 204/157.15 |
| 5,141,911 | 8/1992 | Meunier et al. | 502/159 |
| 5,159,065 | 10/1992 | Sessler et al. | 534/15 |
| 5,162,509 | 11/1992 | Sessler et al. | 534/15 |
| 5,242,797 | 9/1993 | Hirschfeld | 435/6 |
| 5,252,720 | 10/1993 | Sessler et al. | 534/11 |
| 5,272,056 | 12/1993 | Burrows et al. | 435/6 |
| 5,302,714 | 4/1994 | Sessler et al. | 540/472 |
| 5,371,199 | 12/1994 | Therien et al. | 534/11 |
| 5,457,195 | 10/1995 | Sessler et al. | 540/472 |

FOREIGN PATENT DOCUMENTS

| 0111418 | 6/1984 | European Pat. Off. . |
|---|---|---|
| 0196515 | 3/1986 | European Pat. Off. . |
| 0233701 | 1/1987 | European Pat. Off. . |
| WO90/10633 | 9/1990 | European Pat. Off. . |
| WO94/09003 | 4/1994 | WIPO . |

OTHER PUBLICATIONS

Aoyama et al., "Multi–Point Interaction of Phosphate with Protonated Pyridylporphyrin. Discrimination of Monoalkyl and Dialkyl Phosphates," *Chemistry Letters*, 1241–1244 (1991).

Bauer et al., "Sapphyrins: Novel Aromatic Pentapyrrolic Macrocycles," *J Am Chem Soc*, 105:6429–6436 (1983).

Broadhurst and Grigg, "18–and 22–π–Electron Macrocyles Containing Furan, Pyrrole, and Thiophen," *Chemical Communications*, 1480–1482 (1969).

Broadhurst and Grigg, "The Synthesis of 22 π–Electron Macrocycles. Sapphyrins and Related Compounds," *JCS Perkin*, 2111–2116 (1972).

Claude et al., "Binding of Nucleosides, Nucleotides, and Anionic Planar Substrates by Bis–Intercaland Receptor Molecules," *J. Chem Soc. Chem Commun*, 17:1182–1185 (1991).

Cramer et al., "Synthesis and Structure of the Chloride and Nitrate Inclusion Complexes of [16–Pyrimidinium crown–4]", *J Am Chem Soc*, 113:7033–7034 (1991).

Cuellar and Marks, "Synthesis and Characterization of Metallo and Metal–Free Octaalkylphthalocyanines and Uranyl Decaalkylsuperphthalocyanines," *Inorg Chem*, 20:3766–3770 (1981).

Dietrich et al., "Proton Coupled Membrane Transport of Anions Mediated by Cryptate Carriers," *J Chem Soc Chem Comm*, 11:691–692 (1988).

Dixon et al., "Molecular Recognition: Bis–Acylguanidiniums Provide a Simple Family of Receptors for Phosphodiesters," *J Am Chem Soc*, 114:365–366 (1992).

Furuta et al., "Phosphate Anion Binding: Enhanced Transport of Nucleotide Monophosphates Using a Sapphyrin Carrier," *J Am Chem Soc*, 113:6677–6678 (1991).

Furuta et al., "Enhanced Transport of Nucleosides and Nucleoside Analogues with Complementary Base–Pairing Agents," *J Am Chem Soc*, 113:4706–4707 (1991).

Galan et al., "A Synthetic Receptor for Dinucleotides," *J Am Chem Soc*, 113:9424–9425 (1991).

Galan et al., "Selective Complexation of Adenosine Monophosphate Nucleotides by Rigid Bicyclic Guanidinum Abiotic Receptors," *Tetrahedron Letters*, 32(15):1827–1830 (1991).

Harriman et al., "Metallotexaphyrins: A New Family of Photosensitisers for Efficient Generation of Singlet Oxygen," *J Chem Soc Chem Comm*, 314–316 (1989).

Hisatome et al., "Porphyrins Coupled with Nucleoside Bases. Synthesis and Characterization of Adenine–and Thymine–Porphyrin Derivatives," *Chem Lett*, 2251–2254 (1990).

Hosseini et al., "Multiple Molecular Recognition and Catalysis. A Multifunctional Anion Receptor Bearing an Anion Binding Site, an Intercalating Group, and a Catalytic Site for Nucleotide Binding and Hydrolysis," *J Am Chem Soc*, 112:3896–3904 (1990).

Hosseini et al., "Multiple Molecular Recognition and Catalysis. Nucleotide Binding and ATP Hydrolysis by a Receptor Molecule Bearing an Anion Binding Site, an Intercalator Group and a Catalytic Site," *J Chem Soc Chem Comm*, 9:596–598 (1988).

Kimura et al., "A Study of New Bis(macrocyclic polyamine) Ligands as Inorganic and Organic Anion Receptors," *J Org Chem*, 55(1),46–48 (1990).

(List continued on next page.)

Primary Examiner—Mukund J. Shah
Assistant Examiner—Pavanaram K. Sripada
Attorney, Agent, or Firm—Arnold, White & Durkee

[57] ABSTRACT

Sapphyrins are provided having appended functional groups that render the sapphyrin water-soluble. Such water-soluble sapphyrins are useful for photodynamic therapy, for example.

20 Claims, No Drawings

OTHER PUBLICATIONS

Kimura, "Macrocyclic Polyamines as Biological Cation and Anion Complexones—An Application to Calculi Dissolution," 113–141 1990.

Kral et al., "Synthetic Sapphyrin–Cytosine Conjugates: Carriers for Selective Nucleotide Transport at Neutral pH," *J Am Chem Soc*, 114:8704–8705 (1992).

Li and Diederich, "Carriers for Liquid Membrane Transport of Nucleotide 5'-Triphosphates," *J Org Chem*, 47:3449–3454 (1992).

Marks and Stojakowvic, "Large Metal Ion–Centered Template Reactions. Chemical and Spectral Studies of the 'Superphthalocyanine' Dioxocyclopentakis (1–iminoisoindolinato)uranium(VI) and Its Derivatives," *J Am Chem Soc*, 1695–1705 (1978).

Rexhausen and Gossauer, "The Synthesis of a New 22 π–Electron Macrocycle: Pentaphyrin," *Chem Soc Chem Comm*, 6:275 (1983).

Schmidtchen, "A Non–Macrocyclic Host for Binding Organic Phosphates in Protic Solvents," *Tetr Lett*, 30(34):4493–4496 (1989).

Seel and Vogtle, "Molecular Recognition and Transport of Nucleobases—Superiority of Macrobicyclid Host Molecules," *Angew Chem Int Ed Engl*, 30(4):442–444 (1991).

Sessler et al., "Anion Binding: A New Direction in Porphyrin–Related Research," *Pure & Appl Chem*, 65(3):393–398 (1993).

Sessler et al., "Cytosine Amine Derivatives," *J Org Chem*, 47:826–834 (1992).

Sessler et al., "Enhanced Transport of Fluoride Anion Effected Using Protonated Sapphyrin as a Carrier," *J Chem Soc Chem Comm*, 1732–1735 (1991).

Sessler et al. "In vitro photodynamic activity of diprotonated sapphyrin: a 22–π–electron pentapyrrolic prophyrin–like macrocycle," *Chem Abstr*, 112:348–349, 112:194584t (1990).

Sessler et al., "A water–stable gadolinium (III) complex derived from a new pentadentate expanded porphyrin ligand," *Chem Abstr*, 111:720, 111:125716e (1989).

Sessler et al., "Synthetic and Structural Studies of Sapphyrin, a 22–π–Electron Pentapyrrolic 'Expanded Porphyrin'", *J Am Chem Soc*, 112:2810–2813 (1990).

Sessler et al. "An 'Expanded Porphyrin': The Synthesis and Structure of a New Aromatic Pentadentate Ligand," *J Am Chem Soc*, 110:5586–5588 (1988).

Shionoya et al., "Diprotonated Sapphyrin: A Fluoride Selective Halide Anion Receptor,"*J Am Chem Soc*, 114:5714–5722 (1992).

Tabushi et al., "Lipophilic Diammonium Cation Having a Rigid Structure Complementary to Pyrophosphate Dianions of Nucleotides. Selective Extraction and Transport of Nucleotides," *J Am Chem Soc*, 103:6152–6157 (1981).

Tohda et al., "Liquid Membrane Electrode for Guanosine Nucleotides Using a Cytosine–Pendant Triamine Host as the Sensory Element," *Analyt Chem*, 64(8):960–964 (1992).

Iverson et al., "Phosphate Recognition by Sapphyrin. A New Approach to DNA Binding," *J. Am. Chem. Soc.*, 115:11022–11023, 1993.

Sessler et al., "Phosphate Anion Chelation and Base–pairing. Design of Receptors and Carriers for Nucleotides and Nucleotide Analogs," *Supramolec. Chem.*, 1:209–220, 1991.

Sessler et al., "Expanded Porphyrins. Receptors for Cationic, Anionic, and Neutral Substrates," in *Transition Metals in Supramolecular Chemistry*, NATO ASI Series; Fabgrizzi, L. and Poggi, A., Eds., Kluwer, Dorderecht, Series C, 448:391–408, 1994.

Collman et al., "Synthesis of 'Face to Face' Porphyrin Dimers Linked by 5, 15–Substituents: Potential Binuclear Multielectron Redox Catalysts," *JACS*, 103:516–533 (1981).

Franck et al., "Synthese von Geschütztem Nor–und Homoporphobilinogen," *Liebigs Ann. Chem.*, 253–262 (1980).

Grigg et al., "Studies in Furan Chemistry. Part IV[1] 2,2–Bifurans," *J. Chem. Soc.*, 976–981 (1966).

Kambe and Yasuda, "The Potassium Flouride–Catalyzed Reaction. V. Aldol Condensation of Nitroalkanes and Aliphatic Aldehydes," *Bull. Chem. Soc.*, 41(6):1444–1446 (1968).

Tindall, "Esters of Nitroalcohols," *Industrial and Engineering Chemistry*, 33(1):65–66 (1941).

PCT Search Report for PCT/US90/01208, mailed Aug. 2, 1990, printed in USA.

International Search Report for International Application No. PCT/US90/07609, published in Europe.

Barton and Zard, "A New Synthesis of Pyrroles from Nitroalkenes," *J. Chem. Soc., Chem. Commun.*, pp. 1098–1100 (1985), published in Europe.

Broadhurst and Grigg, "New Macrocyclic Aromatic Systems Related to Porphins," *Chem. Commun.*, pp. 23–24 (1969), published in Europe.

Broadhurst and Grigg, "Preparation of Some Sulphur–containing Polypyrrolic Macrocycles. Sulphur Extrusion from a meso–Thiaphlorin," *Chem. Commun.*, pp. 807–809 (1970), published in Europe.

Gossauer, "Syntheses of Some Unusual Polypyrrole Macrocycles," *Bull. Soc. Chem. Belg.*, 92(9):793–809 (1983), published in Europe.

Král et al., "A Covalently Linked Sapphyrin Dimer. A New Receptor for Dicarboxylate Anions," *J. Am. Chem. Soc.*, 117:2953–2954 (1995).

Kus et al., "First Representatives of Porphyrinylnucleotsides," *Tetrahedron Letters*, 5133–5134 (1990).

Maiya et al., "In Vitro Photodynamic Activity of Diprotonated Sapphyrin: a 22–pi–electron Pentapyrrolic Porphyrin–like Macrocycle," *Chem. Abstrs.*, 112:348–349, Abstract #194584t (1990), published in USA.

Sessler et al., "Synthesis and Crystal Structure of a Novel Tripyrrane–Containing Porphyrinogen–like Macrocycle," *J. Org. Chem.*, 52:4394–4397 (1987), published in USA.

Franck et al., "Einfache Biomimetische Porphyrin–Synthesen," *Liebigs Ann. Chem.*, 263–274 (1980).

U.S. Application Ser. No. 08/321,148 (Dkt. No. PHAY:033).

U.S. Application Ser. No. 08/417,940 (Dkt. No. PHAY:036).U.S. Application Serial No. 08/405,275 (Dkt. No. PHAY:043).

U.S. Application Serial No. 08/424,288 (Dkt. No. PHAY:029).

Wardle, "The Surface of Malignant and Virus Transformed Cells," *Cell Surface Science in Medicine and Pathology*, Elsevier Science Publishing Co., Inc., New York, 19:552–561 (1985).

Verlhac & Gaudemer, "Water–Soluble Porphyrins and metalloporphyrins as photosensitizers in aerated aqueous solutions. I. Detection and determination of quantum yield of formation of singlet oxygen," *Nouveau Journal De Chimie*, 8:401–406 (1984).

Král & Sessler, "Molecular Recognition via Base–pairing and Phosphate Chelation, Ditopic and Tritopic Sapphyrin–based Receptors for the Recognition and Transport of Nucleotide Monophosphates," *Tetrahedron*, 51(2):539–554 (1995).

Whitfield et al., "Differntial reactivity of carbohydrate hytdroxyls in glycosylations. II. The likely role of intramolecular hydrogen bonding on glycosylation reactions. Galactosylation of nucleoside 5'–dydroxyls for the syntheses of novel potential anticancer agents," *Can. J. Chem.*, 72:2225–2238 (1994).

Schmidt, "Anomeric–oxygen activation for glycoside synthesis: the trichloroacetimidate method," *Advance in Carbohydrate Chemistry and Biochemistry*, 50:21–123 (1994).

Sessler et al., "Sapphyrins: New Life for an Old Expanded Porphyrin," *Synlett*, 127–134, 1991.

Iverson et al., "Molecular Recognition of Anionic Species by Silica Gel Bound Sapphyrin," *J. Am. Chem. Soc.*, 116:2663–2664 (1994).

Aoyama et al., "Multi–Point Interaction of Phosphates with Protonated Pyridylporphyrin. Discrimination of Monoalkyl and Dialkyl Phosphates," *Chemistry Letters*, 1241–1244 (1991).

Bauer et al., "Sapphyrins: Novel Aromatic Pentapyrrolic Macrocycles," *J Am Chem Soc*, 105:6429–6436 (1983).

Broadhurst and Grigg, "18–and 22–π–Electron Macrocycles Containing Furan, Pyrrole, and Thiophen," *Chemical Communications*, 1480–1482 (1969).

Broadhurst and Grigg, "The Synthesis of 22 π–Electron Macrocycles. Sapphyrins and Related Compounds," *JCS Perkin*, 2111–2116 (1972).

Claude et al., "Binding of Nucleosides, Nucleotides, and Anionic Planar Substrates by Bis–Intercaland Receptor Molecules," *J Chem Soc, Chem Commun*, 17:1182–1185 (1991).

Cramer et al., "Synthesis and Structure of the Chloride and Nitrate Inclusion Complexes of [16–Pyrimidinium crown–4]," *J Am Chem Soc*, 113:7033–7034 (1991).

WATER-SOLUBLE SAPPHYRINS

The government owns rights in the present invention pursuant to NIH grants AI 28845 and AI33577.

This application is a continuation-in-part application of U.S. Ser. No. 07/964 607 filed Oct. 21, 1992, which is a continuation-in-part application of U.S. Ser. No. 07/454, 298, filed Dec. 21, 1989, since issued as U.S. Pat. No. 55,159,065 on Oct. 27, 1992. U.S. Ser. No. 07/964,607 and U.S. Pat. No. 5,159,065 are incorporated by reference herein.

BACKGROUND OF THE INVENTION

1. Field of the Invention

The present invention relates generally to sapphyrin compounds, and particularly, to water-soluble sapphyrin derivatives. Water-soluble sapphyrins include sapphyrins having hydroxy, hydroxyalkyl, oxyalkyl, carboxyamide, polyhydroxy or carbohydrate substituents, for example; and are useful for transport, drug delivery, DNA binding, photodynamic therapy and DNA cleavage.

2. Description of the Related Art

Sapphyrins are large pyrrole-containing macrocyclic analogues of the porphyrins. A number of expanded porphyrin systems are now known. However, only a few fully conjugated examples have been reported that contain more that four pyrrolic subunits, namely the smaragdyrins, sapphyrins, pentaphyrins, hexaphyrins, and superphthalocyanines among others.[1] Sapphyrin, in its generalized substituent-free form, is represented by structure I.

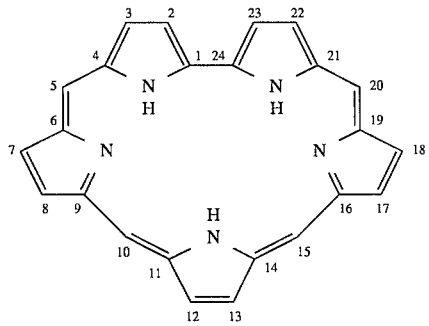

Sapphyrin, first discovered serendipitously by Woodward[2] is one of the more intriguing products to emerge from initial studies directed towards the synthesis of Vitamin $B_{12}$.[2,3] It is a 22 pi-electron pentapyrrolic macrocycle which exhibits an intense Soret-like band at about 450 nm ($CHCl_3$) along with weaker Q-type transitions in the 620 to 690 nm region. These optical properties, along with the presence of a large central cavity which could serve for metal binding, renders sapphyrin useful for certain biomedical applications, including photodynamic therapy (PDT).

In addition to the above, certain expanded porphyrins, including especially those of the sapphyrin series, have been found to act as halide anion chelating agents in both solution and the solid state[4].

Unfortunately, all sapphyrins known at the time of this invention were essentially insoluble in water and were all of such simple character in terms of peripheral substituents, that only those bearing hydrogen or alkyl were known[2,3]. These two deficiencies limited the potential utility of sapphyrins for any applications associated with their use at or near neutral pH and, more generally, any conditions involving partial or complete association with an aqueous environment.

Furthermore, it was recognized that the synthesis of one or more water-soluble sapphyrins would represent a considerable advantage, not only in terms of anion recognition and transport, but also because it would allow for a detailed study of the basic binding phenomena in aqueous media. This latter would be particular true if said water-soluble sapphyrin were neutral in character.

There still remains considerable scope for the design of improved chemotherapeutic compounds which act upon DNA once inside a target cell. Since currently available chemotherapeutic agents have complex structures, or complicated modes of interaction with their targets that preclude systematic improvement, the development of a novel class of DNA binding compounds would open up new avenues for the design of improved therapeutics. In this regard, a class of compounds that can be modified in a number of different ways whilst maintaining their overall structure would be particularly advantageous. The same is true for compounds that can be activated by light, or other means, to produce singlet oxygen or hydroxyl radicals, once bound to DNA. These considerations provided the present inventors with further impetus for the design and synthesis of improved sapphyrins such as those embodied by the present invention.

SUMMARY OF THE INVENTION

The present invention addresses these and other shortcomings in the prior art through the synthesis of several water-soluble sapphyrin derivatives.

The present invention provides sapphyrin derivatives having the structure:

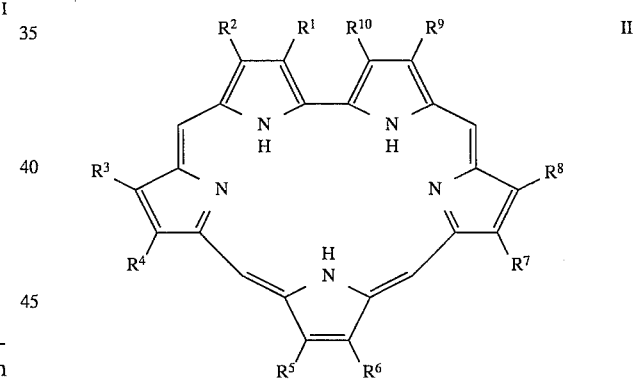

wherein each of $R^1$–$R^{10}$ are independently hydrogen, alkyl, alkene, alkyne, halide, alkylhalide, hydroxyalkyl, hydroxyalkylamido, glycol, polyglycol, thiol, thioalkyl, aminoalkyl, carboxyalkyl, carboxyamidealkyl, oxyalkyl, alkoxyalkyl, aryloxyalkyl, oxyhydroxyalkyl, alkyloxycarbonyl, aryloxycarbonyl, aldehyde, ether, ketone, carboxylic acid, phosphate, phosphonate, sulfate, phosphate substituted alkyl, phosphonate substituted alkyl, or sulfate substituted alkyl, such that the total number of carbon atoms in each substituent R is less than or equal to 100.

The novel aspect of the water-soluble sapphyrins is that at least one of $R^1$–$R^{10}$ is of the formula $(CH_2)_n$—A—$(CH_2)_m$—B, where A is alkyl having from 1–4 carbon atoms, oxy, sulfide, amide, carbonyl, alkenyl, alkynyl, alkylhalide, hydroxyalkyl, glycol, polyglycol, alkylthiol, substituted alkyl, phosphate, phosphonate, sulfate, phosphate substituted alkyl, phosphonate substituted alkyl, sulfate substituted alkyl, carboxy, carboxyamide, ester, thiol-substituted carboxyamide, or derivatized carboxyamide; B is hydroxy, hydroxyalkyl, oxyalkyl, carboxy, carboxyalkyl, glycol, polyglycol, thiol, aminoalkyl, phosphate, phosphonate, sulfate, phosphate substituted alkyl, phosphonate substituted alkyl, sulfate substituted alkyl, substituted hydroxyalkyl, saccharide, saccharide derivative, or polysaccharide; and n and m are independently an integer from 0 to 4.

Derivatized carboxyamide may be described as having the formula $CONR^{11}R^{12}$, where $R^{11}$ and $R^{12}$ may be separately and independently H, alkyl, alkyl halide, hydroxyalkyl, glycol, polyglycol, alkylthiol, or amide.

In a preferred embodiment, A is alkyl having 1–4 carbon atoms, oxy, sulfide, amide, carbonyl, carboxy, carboxyamide, ester, thiol-substituted carboxyamide, or derivatized carboxyamide; and B is hydroxy, hydroxyalkyl, saccharide, saccharide derivative or polysaccharide. In another preferred embodiment, B is hydroxyalkyl, most preferably, hydroxymethyl, hydroxyethyl, hydroxypropyl, or hydroxybutyl. In a more preferred embodiment, a water-soluble sapphyrin has $R^2$, $R^4$–$R^7$, and $R^9$ selected from the substituents of Tables 2 or 3. Most preferably, $R^4$, $R^5$, or $R^7$ is of the formula $(CH_2)_n$—A—$(CH_2)_m$—B, where B is hydroxyalkyl or saccharide. Particular water-soluble sapphyrins are exemplified by sapphyrins A1–A27 of Table 2 or B1–B8 of Table 3.

In further preferred embodiments of the present invention, A is carboxyamide and B is hydroxyalkyl or saccharide, A is oxy and B is oxyalkyl, A is alkenyl and B is hydroxy.

In another preferred embodiment of the water-soluble sapphyrins of the present invention, B is saccharide or saccharide derivative, and more preferably, the saccharide or saccharide derivative is selected from those set forth in Table 1. Where B is a polysaccharide, the polysaccharide is preferably chitosan, alginic acid, hyaluronic acid, or dextran.

Water-soluble sapphyrins are particularly desirable where one would like to exploit the various surprising properties of the sapphyrin macrocycle in connection with human or animal applications. "Water-soluble" means soluble in aqueous fluids to about 1 mM or better. Water-solubility may be achieved by hydroxylation of the sapphyrin macrocycle, and the nature of the hydroxylation is not particularly critical so long as at least one, and preferably two, or three hydroxyl groups per sapphyrin macrocycle are incorporated into the structure.

One means for introducing hydroxyl groups into the sapphyrin macrocycle structure is simply through the addition of hydroxyalkyl substituents to the basic sapphyrin macrocycle unit, wherein the added substituents include one or more hydroxyl groups within their structures. An alternative means of achieving polyhydroxylation is through the addition of sugar moieties such as a saccharide, polysaccharide, saccharide derivative or aminosaccharide, to the sapphyrin macrocycle structure. In such cases, it has been found that the addition of a single saccharide molecule to a sapphyrin macrocycle will achieve a degree of water solubility. These structures are referred to broadly herein as simply sapphyrin-saccharide compounds or derivatives. The nature of the saccharide is not particularly critical to the achievement of water solubility.

Water-soluble sapphyrin derivatives are of interest in a variety of applications including photodynamic therapy (PDT), DNA recognition and modification, cellular recognition, and transport. In regard to PDT, water-soluble sapphyrins may be used as photosensitization agents for the generation of cytotoxic singlet $O_2$ in vitro, ex vivo or in vivo; as well as photodynamic inactivation of infectious agents having membranous envelopes. As such they may be employed in the photo-eradication of cell-free viruses from blood samples, such as, for example, the hepatitis viruses HBV and NANB, and especially HIV-1. In this process, sapphyrin localizes selectively at or near the morphologically characteristic viral envelope. Upon photoirradiation, it catalyzes the formation of highly reactive singlet oxygen which, in turn, destroys the essential membrane envelope thus killing the virus and eliminating its infectivity; see U.S. Pat. No. 5,041,078, incorporated herein by reference.

The search for compounds for use in in vivo cellular transport and uptake, where diffusion across a membrane is involved, led the inventors to synthesize and characterize the range of novel water-soluble sapphyrin derivatives described herein. It is contemplated that water-soluble sapphyrin derivatives will have utility in both photophysical and biological embodiments. For example, it is envisioned that these new sapphyrins will have improved solubility and/or phosphate anion chelation properties, rendering them of use in protocols such as anti-viral transport and RNA/DNA recognition and binding.

DETAILED DESCRIPTION OF THE PREFERRED EMBODIMENTS

The synthesis of various sapphyrins and uses thereof have been previously reported[2-6,7,8], see also U.S. Pat. Nos. 5,159,065, 5,120,411, 5,041,078 and 5,302,714; each of these references is incorporated herein by reference. Structural information is available for a limited number of alkyl-substituted sapphyrins[4]. The present invention concerns water-soluble sapphyrins that overcome known deficiencies associated with extant sapphyrins. This is because all sapphyrins known at the time of this invention were insoluble in aqueous media at or near neutral pH. Thus, the sapphyrins known prior to the present invention were incapable of forming well characterized, water-soluble complexes with phosphorylated entities, including DNA, RNA, nucleotides, nucleotide analogues, and simple phosphate and phosphonate monoesters, at or near neutral pH.

In addition, all sapphyrins known at the time of this invention were recognized to be quite limited in terms of their substitution patterns, bearing only alkyl groups in the so-called β-positions. Furthermore, this same lack of substituent versatility meant that sapphyrin systems carrying potentially reactive side chains were completely unknown, and this too was recognized as limiting the utility of those few sapphyrins known to be extant at the time of this invention. Thus, the inventors felt it worthwhile to prepare water-soluble sapphyrins.

Representative examples of alkanes useful as alkyl group substituents of water-soluble sapphyrins include methane, ethane, straight-chain, branched or cyclic isomers of propane, butane, pentane, hexane, heptane, octane, nonane and decane, with methane, ethane and propane being preferred. Representative examples of alkenes useful as alkenyl group substituents include ethene, straight-chain, branched or cyclic isomers of propene, butene, pentene, hexene, heptene, octene, nonene and decene, with ethene and propene being preferred. Representative examples of alkynes useful as alkynyl group substituents include ethyne, straight-chain, branched or cyclic isomers of propyne, butyne, pentyne, hexyne, heptyne, octyne, nonyne and decyne, with ethyne and propyne being preferred. Representative examples of substituted alkyls include alkyls substituted by one or more functional groups as described herein.

Among the halide substituents, chloride, bromide, fluoride and iodide are contemplated in the practice of this invention. Representative examples of alkylhalides used in this invention include halides of methane, ethane, propane, butane, pentane, hexane, heptane, octane, nonane and decane, with halides, preferably chlorides or bromides, of methane, ethane and propane being preferred.

"Hydroxyalkyl" means alkyl groups having hydroxyl groups attached. Representative examples of hydroxyalkyls include alcohols of methane, ethane; straight-chain, branched or cyclic isomers of propane, butane, pentane, hexane, heptane, octane, nonane and decane, with alcohols of methane, ethane or propane being preferred. "Hydroxyalkyl" is meant to include glycols and polyglycols; diols of ethane, straight-chain, branched or cyclic isomers of propane, butane, pentane, hexane, heptane, octane, nonane and decane, with diols of ethane or propane being preferred; polyethylene glycol, polypropylene glycol and polybutylene glycol as well as polyalkylene glycols containing combinations of ethylene, propylene and butylene.

"Oxyalkyl" means alkyl groups attached to an oxygen. Representative examples of oxyalkyls include the alkyl groups as herein described having ether linkages. The number of repeating oxyalkyls within a substituent may be up to 100, preferably is from 1–10, and more preferably, is 2–3. A preferred oxyalkyl is $O(CH_2CH_2O)_x CH_3$ where $x=1-100$, preferably 1–10, and more preferably, 2–3. "Oxyhydroxyalkyl" means alkyl groups having ether or ester linkages, hydroxyl groups, substituted hydroxyl groups, carboxyl groups, substituted carboxyl groups or the like.

Representative examples of thioalkyls include thiols of ethane, thiols of straight-chain, branched or cyclic isomers of propane, butane, pentane, hexane, heptane, octane, nonane and decane, with thiols of ethane (ethanethiol, $C_2H_5SH$) or propane (propanethiol, $C_3H_7SH$) being preferred. Sulfate substituted alkyls include alkyls as described above substituted by one or more sulfate groups, a representative example of which is diethyl sulfate (($C_2H_5)_2SO_4$).

Representative examples of phosphates include phosphate or polyphosphate groups. Representative examples of phosphate substituted alkyls include alkyls as described above substituted by one or more phosphate or polyphosphate groups. Representative examples of phosphonate substituted alkyls include alkyls as described above substituted by one or more phosphonate groups.

Representative examples of carboxy groups include carboxylic acids of the alkyls described above as well as aryl carboxylic acids such as benzoic acid. Representative examples of carboxyamides include primary carboxyamides ($CONH_2$), secondary ($CONHR'$) and tertiary ($CONR'R''$) carboxyamides where each of R' and R'' is a functional group as described herein.

Representative examples of useful amines include a primary, secondary or tertiary amine of an alkyl as described hereinabove. Hydroxyalkylamido refers to a substituent having a hydroxyalkyl and an amine group; the amine may be primary, secondary or tertiary.

Saccharide includes oxidized, reduced or substituted saccharides, including those of Table 1, for example, derivatives such as acetals, amines, and phosphorylated sugars, oligosaccharides, as well as open chain forms of various sugars, and the like. Examples of amine-derivatized sugars are galactosamine, glucosamine, sialic acid and D-glucamine derivatives such as 1-amino-1-deoxysorbitol. The saccharides employed may be either D or L forms and may also be either α or β forms. The use of modified saccharides is also envisioned, such as those including, for example, phosphate, methyl or amino groups. It is contemplated that preferred saccharides for use in accordance herewith will include, for example, glucose, glucosamine, galactose, galactosamine and mannose.

TABLE 1

| Examples of Saccharides and Saccharide Derivatives | |
|---|---|
| Ribose | Fructose |
| Arabinose | Sorbose |
| Xylose | Tagatose |
| Lyxose | Fucose |
| Allose | |
| Altrose | Methylglucoside |
| Glucose | Glucose 6-phosphate |
| Mannose | |
| Gulose | N-Acetylgalactosamine |
| Idose | N-Acetylglucosamine |
| Galactose | Sialic Acid |
| Talose | Chitosan |
| Ribulose | Alginic Acid |
| Xylulose | |
| Psicose | |
| Sucrose | |
| Lactose | |
| Maltose | |

"Carboxyamidealkyl" means alkyl groups with carboxyamide groups, optionally having secondary or tertiary amide linkages, or amide substituted ethers, ester linkages, tertiary amide linkages removed from the ether or the like. Carboxyalkyl means alkyl groups having carboxyl groups.

For the sapphyrins of the present invention, oxyhydroxyalkyl may be alkyl having independently hydroxy substituents and ether branches or may be $C_{(n-x)}H_{((2n+1)-2x)}O_xO_y$ or $OC_{(n-x)}H_{((2n+1)-2x)}O_xO_y$ where n is a positive integer from 1 to 10, x is zero or a positive integer less than or equal to n, and y is zero or a positive integer less than or equal to $((2n+1)-2x)$.

The oxyhydroxyalkyl or saccharide may be $C_nH_{((2n+1)-q)}O_yR^a_q$, $OC_nH_{((2n+1)-q)}O_uR^a_q$ or $(CH_2)_nCO_2R^a$ where n is a positive integer from 1 to 10, y is zero or a positive integer less than $((2n+1)-q)$, q is zero or a positive integer less than or equal to $2n+1$, $R^a$ is independently. H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to $((2m+1)-2w)$, R is H, alkyl hydroxyalkyl or $C_mH_{((2m+1)-r)}O_zR^b_r$ where m is a positive integer from 1 to 10, z is zero or a positive integer less than $((2m+1)-r)$, r is zero or a positive integer less than or equal to $2m+1$, and $R^b$ is independently H, alkyl, hydroxyalkyl, or saccharide.

Carboxyamidealkyl may be alkyl having secondary or tertiary amide linkages or $(CH_2)_nCONHR^a$, $O(CH_2)_nCONHR^a$, $(CH_2)_nCON(R^a)_2$, or $O(CH_2)_nCON(R^a)_2$ where n is a positive integer from 1 to 10, $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to $((2m+1)-2w)$, R is H, alkyl, hydroxyalkyl or $C_mH_{((2m+1)-r)}O_zR^b_r$ where m is a positive integer from 1 to 10, z is zero or a positive integer less than $((2m+1)-r)$, r is zero or a positive integer less than or equal to $2m+1$, and $R^b$ is independently H, alkyl, hydroxyalkyl, or saccharide.

The carboxyalkyl may be alkyl having a carboxyl substituted ether, an amide substituted ether or a tertiary amide removed from an ether or $C_nH_{((2n+1)-q)}O_yR^c_q$ or $OC_nH_{((2n+1)-q)}O_yR^c_q$ where n is a positive integer from 1 to 10; y is zero or a positive integer less than ((2n+1)–q), q is zero or a positive integer less than or equal to 2n+1, $R^c$ is $(CH_2)_nCO_2R^d$, $(CH_2)_nCONHR^d$ or $(CH_2)_nCON(R^d)_2$ where n is a positive integer from 1 to 10; $R^d$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to ((2m+1)–2w), R is H, alkyl, hydroxyalkyl, or $C_mH_{((2m+1)-r)}O_zR^b_r$ where m is a positive integer from 1 to 10, z is zero or a positive integer less than ((2m+1)–r), r is zero or a positive integer less than or equal to 2m+1, and $R^b$ is independently H, alkyl, hydroxyalkyl, or saccharide.

"Water-soluble" sapphyrins means sapphyrins that are soluble in aqueous fluids to about 1 mM or better. Water-soluble sapphyrins may retain lipophilicity. "Retaining lipophilicity" means having greater affinity for lipid-rich tissues or materials than surrounding nonlipid-rich tissues or materials and, in the case of viruses in suspension, the term means having affinity for the membranous coat of the virus. "Lipid-rich" means having a greater amount of triglyceride, cholesterol, fatty acids or the like.

Generally speaking, the water-soluble sapphyrin derivatives of this invention will include at least one, two or three hydroxy groups, such as can be supplied by a variety of different polyhydroxy groups, or a single sugar residue. These groups include a variety of distinct molecules, such as, for example, the compounds represented by compounds A1–A27 in Table 2 and B1–B8 in Table 3, or substituted derivatives thereof.

Water-soluble sapphyrin derivatives may be based on one, two, or more (poly)hydroxyalkylamido units attached to the macrocyclic periphery or, alternatively, be based on the attachment of one, two, or more hydroxyalkyl groups to the macrocycle, the hydroxyalkyl groups including from one to six hydroxy moieties or, alternatively, be based on the attachment of saccharide or derivatized saccharide moieties to the macrocycle. It will be understood that a wide variety of different, and yet analogous, substituted derivatives may be prepared in accordance herewith. Water-soluble sapphyrins may be prepared from an activated form of a sapphyrin acid (acid chloride, mixed anhydride, O-acylurea derivative, N-acylimidazole) and polyhydroxyamines.

Preferred substituent groups for $R^2$, $R^4$–$R^7$ and $R^9$ of sapphyrins are listed in Tables 2 and 3. Preferred water-soluble sapphyrins are listed as compounds A1–A27 of Table 2 and compounds B1–B8 of Table 3.

TABLE 2

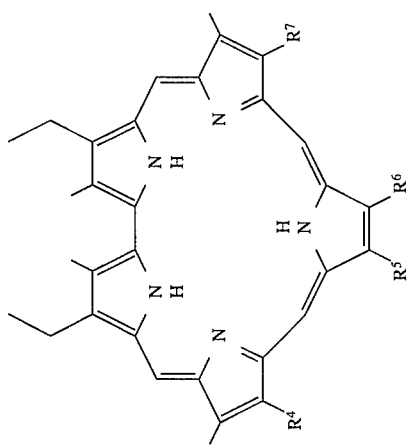

| Cpd. | R⁴ | R⁵ | R⁶ | R⁷ |
|---|---|---|---|---|
| A1 | $CH_2CH_2CON(CH_2CH_2OH)_2$ | $CH_2CH_3$ | $CH_2CH_3$ | $CH_2CH_2CON(CH_2CH_2OH)_2$ |
| A2 | $CH_2CH_2OH$ | $CH_2CH_3$ | $CH_2CH_3$ | $CH_2CH_2OH$ |
| A3 | $CH_2CH_2CONHC(CH_2OH)_3$ | $CH_2CH_3$ | $CH_2CH_3$ | $CH_2CH_2CONHC(CH_2OH)_3$ |
| A4 | $CH_2CH_2CONHCH_2(CHOH)_4CH_2OH$ | $CH_2CH_3$ | $CH_2CH_3$ | $CH_2CH_2CONHCH_2(CHOH)_4CH_2OH$ |
| A5 | $CH_2CONHCH_2(CHOH)_4CH_2OH$ | $CH_2CH_3$ | $CH_2CH_3$ | $CH_2CONHCH_2(CHOH)_4CH_2OH$ |
| A6 | $CH_2CH_2CONH$-sugar | $CH_2CH_3$ | $CH_2CH_3$ | $CH_2CH_2CONH$-sugar |
| A7 | $CH_2CH_2CONH$-sugar | $CH_2CH_3$ | | $CH_2CH_2COOH$ |

TABLE 2-continued

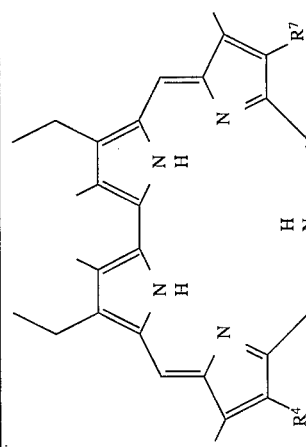

| Cpd. | R⁴ | R⁵ | R⁶ | R⁷ |
|---|---|---|---|---|
| A8 | $CH_2CH_3$ | $CH_2CH_2CONH$-(sugar) | $CH_3$ | $CH_2CH_3$ |
| A9 | $CH_2CH_2OH$ | $CH_2CH_2OH$ | $CH_2CH_2OH$ | $CH_2CH_2OH$ |
| A10 | $CH_2CH(CH_2OH)_2$ | $CH_2CH_3$ | $CH_2CH_3$ | $CH_2CH(CH_2OH)_2$ |
| A11 | $CH_2CH=C(OH)_2$ | $CH_2CH_3$ | $CH_2CH_3$ | $CH_2CH=C(OH)_2$ |
| A12 | $O(CH_3CH_2O)_3CH_3$ | $CH_2CH_3$ | $CH_2CH_3$ | $O(CH_3CH_2O)_3CH_3$ |
| A13 | $CHOHCH_2OH$ | $CH_2CH_2OH$ | $CH_2CH_2OH$ | $CHOHCH_2OH$ |
| A14 | $CH_2CH_2COOCH_2CH_2OH$ | $CH_2CH_3$ | $CH_2CH_3$ | $CH_2CH_2COOCH_2CH_2OH$ |
| A15 | $CH_2CH_2OPO(OH)_2$ | $CH_2CH_2OH$ | $CH_2CH_2OH$ | $CH_2CH_2OPO(OH)_2$ |
| A16 | $CH_2CH_2OH$ | $CH_2CH_2OH$ | $CH_2CH_2OH$ | $CH_2CH_2OH$ |
| A17 | $O(CH_2CH_2O)_3CH_3$ | $CHOHCH_2OH$ | $CHOHCH_2OH$ | $O(CH_2CH_2O)_3CH_3$ |
| A18 | $CH_2CH_2CONHCH_2(CHOH)_4CH_2OH$ | $CH_2OCH_3$ | $CH_2OCH_3$ | $CH_2CH_2CONHCH_2(CHOH)_4CH_2OH$ |
| A19 | $CH_2CH_2COOH$ | $CH_2CH_3$ | $CH_2CH_3$ | $CH_2CH_2COOH$ |
| A20 | $CH_2CH_2COOCH_3$ | $CH_2CH_3$ | $CH_2CH_3$ | $CH_2CH_2COOCH_3$ |
| A21 | (sugar) | $CH_2CH_3$ | $CH_2CH_3$ | (sugar) |

TABLE 2-continued

| Cpd. | R⁴ | R⁵ | R⁶ | R⁷ |
|---|---|---|---|---|
| A22 | A21a: R = Bz<br>A21b: R = Ac<br>A21c: R = H<br>(sugar-CH₂CH₂CONH) | CH₂CH₃ | CH₂CH₃ | A21a: R = Bz<br>A21b: R = Ac<br>A21c: R = H<br>(sugar-CH₂CH₂CONH) |
| A23 | A22a: R = Ac<br>A22b: R = H<br>CH₂CH₃<br>A23a: X = OH<br>A23b: X = D-galactosamine<br>A23c: X = D-glucosamine<br>A23d: x = D-mannosamine<br>A23e: x = L-mannosamine<br>A23f: X = chitosan | CH₂CH₂COX | CH₃ | A22a: R = Ac<br>A22b: R = H<br>CH₂CH₃ |
| A24 | CH₂CH₂COOH | CH₂CH₃ | CH₂CH₃ | CH₂CH₂COOCH₃ |
| A25 | CH₂COOH | CH₂CH₃ | CH₂CH₃ | CH₂COOH |

TABLE 2-continued
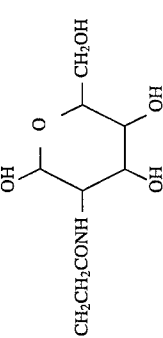
| Cpd. | R⁴ | R⁵ | R⁶ | R⁷ |
|---|---|---|---|---|
| A26 | 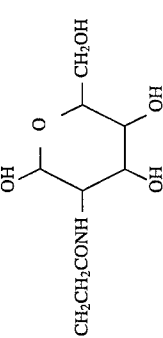 | $CH_2CH_3$ | $CH_2CH_3$ | $CH_2CH_2COOCH_3$ |
| A27 | $CH_2CH_3$ | $CH_2CH_2CONH-$ $CH_2CH_2NH-X$ A27a: X = alginic acid A27b: X = hyaluronic acid A27c: X = dextran A27d: X = H | $CH_3$ | $CH_2CH_3$ |

TABLE 3

| Cpd. | R² | R⁴ | R⁷ | R⁹ |
|---|---|---|---|---|
| B1 | CHOHCH₂OH | O(CH₂CH₂O)₃CH₃ | O(CH₂CH₂O)₃CH₃ | CHOHCH₂OH |
| B2 | CH₂CH₂OH | CH₂CH₂COOCH₂CH₂OH | CH₂CH₂COOCH₂CH₂OH | CH₂CH₂OH |
| B3 | CH₂CH₂OH | CH₂CH₂OH | CH₂CH₂OH | CH₂CH₂OH |
| B4 | CH₂CH₂OH | CH₂CH₂OH | CH₂CH₂COOH | CH₂CH₂OH |
| B5 | CH₂CH₂OH | CH₂CH₂CH₂OPO(OH)₂ | CH₂CH₂OH | CH₂CH₂OH |
| B6 | CH₂CH₃ | CH₂CONHCH₂(CHOH)₄CH₂OH | CH₂CH₂COOH | CH₂CH₃ |
| B7 | CH₂CH₃ | CH₂CONHCH₂(CHOH)₄CH₂OH | CH₂NHC(O)CH₂Br | CH₂CH₃ |
| B8 | CH₂CH₃ | CH₂CONHCH₂(CHOH)₄CH₂OH | CH₂OC(O)CH₂Br | CH₂CH₃ |

The synthesis of representative compounds A21 and A22 involve compounds that are connected via glycoside bonds and are obtained starting from dihydroxysapphyrin and α-D-acetobromoglucose as precursors, and using silver triflate in dichloromethane to effect coupling; or, a trichloroacetimidate method can be used to effect this coupling[11]. Other substituents are connected via amide bonds. These later materials are obtained starting from sapphyrin(bis)acid chloride and 1,3,4,6-tetra-O-acetyl-2-amino-2-deoxy-α-D-glucopyranose (tetraacetyl-D-glucosamine). After removing the protecting groups from the sugar moieties, the desired water-soluble sapphyrin derivatives are obtained.

The efficiency of compounds A21c and A22b for singlet oxygen generation was found to be 11% (in comparison with ZnTPPS₄)[12]. These water-soluble sapphyrins A21c and A22b thus have utility as a cellular targeting agent. As is generally known, glycoconjugates have important roles in the control of cell division and intercellular association. Changes in the biochemical and organizational structures occur during malignant transformation[9]. Therefore, it may be therapeutically advantageous to alter or inhibit the biosynthesis of these tumor cell surface constituents. This might result in tumor cell death caused by the inhibition of the biosynthesis of vital membrane components. In this regard, D-glucosamine derivatives have been proven to be efficient inhibitors of tumor growth[10].

It is envisioned that differential tumor toxicity and specific organ targeting can be achieved with different sapphyrin saccharide derivatives. For instance, modified sugars such as e.g., Glc-NAc can be included within the scope of substituents that can be appended to the sapphyrin core. All that would be needed is to start with an activated sapphyrin and 2-acetamido-2-deoxy-3,4,6-tri-O-acetyl-β-D-glucopyranosylamine. Similarly, other saccharides having cell or tissue specific receptors may be appended to sapphyrins for molecular targeting. Examples include galactose for binding to the asialoglycoprotein receptor on hepatocytes for targeting liver, mannose or fucose for receptors on bone marrow and alveolar macrophage, glycosylated ara-C for ovarian cancer cells and lectins for lymphocytes. The synthesis and use of these and other related systems are thus considered to fall within the scope of the present invention.

For the above-described uses, water-soluble sapphyrins are provided as pharmaceutical preparations. A pharmaceutical preparation of a sapphyrin may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining a water-soluble sapphyrin of the present invention and the pharmaceutically acceptable carriers are then easily administered in a variety of dosage forms such as injectable solutions.

For parenteral administration, solutions of the sapphyrin in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy use with a syringe exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars such as mannitol or dextrose or sodium chloride. A more preferable isotonic agent is a mannitol solution of about 2–8% concentration, and, most preferably, of about 5% concentration. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like that are acceptable for use in the human body. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. For example, other macrocyclic, positively-charged entities can be envisioned as binding to phosphate-containing species such as nucleotides, oligonucleotides and DNA by means of the same or similar oriented electrostatic interactions described herein.

EXAMPLE 1

Synthesis of Polyhydroxysapphyrins

Preparation of 3,12,13,22-tetraethyl-8,17 bis[di (hydroxyethyl)aminocarbonylethyl]-2,7,18,23-tetramethylsapphyrin, A1. Sapphyrin bis acid A19 (synthesized as described in references 1, 6 and U.S. Pat. No. 5,302,714 where $R_2$ ($R_4$ in current scheme) is $CH_2COOH$) (66 mg, 0.1 mmol) was dissolved/suspended in dry dichloromethane (30 ml) and 0.5 ml oxalylchloride and 1 drop of DMF were added. The reaction mixture was stirred at room temperature for 3 hours, then evaporated to dryness. The resulting sapphyrin bis acid chloride was dissolved in dry dichloromethane (20 ml) and slowly added under argon to the solution of diethanolamine (52.5 mg, 0.5 mmol) in dry dichloromethane (30 ml), which contained also 5 mg of 4-dimethylaminopyridine and 0.2 ml pyridine. The reaction mixture was stirred at room temperature for 24 hours and then washed with brine, which contained 5% hydrochloric acid. The water phase was washed 3 times with dichloromethane containing 20% methanol. The combined organic extracts were dried over sodium sulfate and evaporated. Crystallization from ethanolhexane (1:3) gave 75 mg (86.9%) of product A1.

$^1$H NMR (300 MHz, $CDCl_3$) δ: −5.13 (2H, s, NH), −4.95 (1H, s, NH), −4.78 (2H, s, NH), 2.18 (4H, t, $CH_2CH_3$), 2.20 (4H, t, $CH_2CH_3$), 2.24 (4H, t, $CH_2CH_3$), 2.88 (8H, t, $NCH_2CH_2OH$), 2.94 (8H, t, $NCH_2CH_2OH$), 3.56 (4H, t, $CH_2CH_2CON$), 4.07 (6H, s, $CH_3$), 4.25 (6H, s, $CH_3$), 4.49 (2H, q, $CH_2CH_3$), 4.52 (2H, q, $CH_2CH_3$), 4.79 (2H, q, $CH_2CH_3$), 5.15 (2H, q, $CH_2CH_3$), 5.30 (4H, t, $CH_2CH_2CON$), 6.05 (4H, br s, OH), 11.66 (2H, s, meso-H), 11.78 (2H, s, meso-H). FAB MS m/e (rel. intensity) 863 (98, [MH]$^+$), 864 (78, [MH$_2$]$^+$), 862 (56,[M]$^+$). HRMS Calcd for $C_{50}H_{68}N_7O_6$:862.520676. Found 862.523102 UV/VIS ($H_2O$): $\lambda_{max}$ 410.5, 621.0, 672.0.

Preparation of 3,12,13,22-tetraethyl-8,17-bis{[tris (hydroxymethyl)methylamino]-carbonylethyl}-2,7,18,23-tetramethylsapphyrin, A3. Sapphyrin bis acid structure A19 (66 mg, 0.1 mmol) was dissolved in dry tetrahydrofuran (20 ml) and 1,1'-carbonyldiimidazole (33 mg, 0.2 mmol) was added and the solution was stirred at room temperature for 1 hour. A solution of tris(hydroxymethyl)aminomethane (24.2 mg, 0.2 mmol) in 3 ml of water was added. The reaction mixture was stirred for 12 hours and the imidazole was filtered off; the solvent was evaporated in vacuo and the product crystallized from a mixture of methanol-dichloromethane (1:10). The yield of product A3 was 73 mg (81.5%). FAB MS m/e (rel. intensity) 896 (100,[M]$^+$), 897 (60, [MH]$^+$). HRMS: Calcd. $C_{50}H_{69}N_7O_8$ 895.52072. Found 895.52099. UV/VIS ($H_2O$): $\lambda_{max}$ 412,622,673.

EXAMPLE 2

Synthesis of Sapphyrin Diglycosides

Sapphyrin mono- and diglycosides were prepared by the glycosylation of sapphyrin alcohols with α-D-acetobromoglucose and α-D-acetobromogalactose with a silver catalyst. The most advantageous catalyst was found to be silver triflate, although silver tetrafluoroborate and silver carbonate also gave very good results. With polyalcohols it is possible to determine the conversion to glycosides by the molar ratio alcohol-halogenose/silver catalyst. The inventors were able to introduce 1 or 2 sugar units as a function of the molar ratio of hydroxy groups/halogenose/silver catalyst. The trichloroacetimidate method can also be used to effect the coupling of a sapphyrin and a glycoside.[11]

Preparation of 3,12,13,22-Tetraethyl-8,17-di(hydroxypropyl)-2,7,18,23-tetramethylsapphyrin A2. In accordance with the general optimized procedure for the production of substituted sapphyrins[4a], 4,4'-diethyl-5,5'-diformyl-3,3'-dimethyl-2,2'-bipyrrole (544 mg, 2.0 mmol) and 2,5-bis(5-carboxy-3-hydroxypropyl-4-methylpyrrol-2-ylmethyl)-3,4-diethylpyrrole (1.028 g, 2.0 mmol) were dissolved in absolute ethanol (2.0 l) under heating. The reaction mixture was allowed to cool to room temperature and p-toluenesulfonic acid monohydrate (1.5 g) was added. Air was vigorously bubbled through the reaction mixture for 4 days.

The ethanol solvent was then removed using a rotorary evaporator and the product isolated by column chromatography on silica gel using dichloromethane containing methanol (1–5%) as the eluent. The bis hydrochloride salt was prepared by washing a dichloromethane solution of this sapphyrin with 1N HCl to give a 78% (1.151 g) yield of the diprotonated product. $^1$H NMR for A2—2HCl (300 MHz, CDCl$_3$): δ–4.93 (2H, s, NH), –4.63 (1H, s, NH), –4.30 (2H, s, NH), 2.07 (6H, t, CH$_2$CH$_3$), 2.16 (6H, t, CH$_2$CH$_3$), 2.76 (4H, pentet, CH$_2$CH$_2$CH$_2$OH), 4.03 (6H, s, CH$_3$), 4.06 (4H, t, CH$_2$CH$_2$CH$_2$OH), 4.20 (6H, s, CH$_3$), 4.59 (4H, q, CH$_2$CH$_3$), 4.68 (4H, q, CH$_2$CH$_3$), 4.77 (4H, t, CH$_2$CH$_2$CH$_2$OH), 11.59 (2H, s, meso-H), 11.66 (2H, s, meso-H); $^{13}$C NMR (80 MHz, CDCl$_3$): δ 13.15, 16.19, 17.84, 19.14, 21.85, 21.94, 25.04, 36.94, 62.25, 91.17, 97.53, 127.30, 128.38, 128.77, 131.77, 133.65, 134.46, 138.63, 140.54, 142.26, 143.88; UV-Vis (free base in MeOH): λ$_{max}$ (ε) 443 (230 000), 573 (1 800), 618 (6 400), 669 (6 800) HRMS FAB calcd for C$_{42}$H$_{54}$N$_5$O$_2$ (MH$^+$) 660.427751, obsd 660.428736; Anal. Calcd for C$_{42}$H$_{55}$N$_5$O$_2$Cl$_2$.H$_2$O: C, 67.19; H, 7.65; N, 9.33; Cl, 9.44. Found: C, 67.25; H, 7.61; N, 9.41; Cl, 9.35.

Preparation of 8,17-di(tetraacetate-α,β-D-glucopyranoxypropyl)-3,12,13,22-tetraethyl-2,7,18,23-tetramethylsapphyrin, A21b. 3,12,13,22-Tetraethyl-2,7,18,23-tetramethyl-8,17-di(hydroxypropyl) sapphyrin A2 (132 mg, 0.2 mmol) was dried with silver triflate (0.2569 g, 1 mmol) and barium carbonate (0.5 g) for 2 hours at 20° C./1.32 mm Hg in an apparatus equipped with a septum. The apparatus was flushed with argon (2×) and dry dichloromethane (50 ml) was added through the septum. After dissolution, the mixture was cooled to –45° C. and a solution of α-D-glucopyranosylbromide tetraacetate (0.411 g 1 mmol) in dichloromethane (20 ml) was gradually added through septum under stirring. The reaction mixture was stirred at –45° C. for 1 hour, then allowed to warm to room temperature with exclusion of light and stirred for 8 hours. The reaction mixture was diluted with 50 ml of dichloromethane, and filtered with celite; the filtrate was washed with a saturated solution of sodium hydrogen carbonate and water, dried over sodium sulfate and the solvent was evaporated. Pure product was obtained by column chromatography on silica gel with dichloromethane with 4% of methanol as a eluent. The yield of product A21b was 250 mg (94.7%). $^1$H NMR spectrum (300 MHz, CDCl$_3$): δ–6.21–6.07, –5.81, –5.75, 2.03, 2.05, 2.11, 2.13, 2.16, 2.28, 2.31, 3.09, 4.11, 4.17, 4.24, 4.33, 4.51, 4.53, 4.72, 4.74, 5.29, 11.59, 11.66. FAB MS, m/e (rel. intensity): 1321 (90, [MH]$^+$), 1322 (56, [MH$_2$]$^+$), 1320 (45, [M]$^+$). HRMS Calcd. for C$_{70}$H$_{89}$N$_5$O$_{20}$ 1319.6100. Found 1320.617916 ([MH]$^+$).

The same experimental procedure was used for the preparation of tetraacetylgalactose and tetraacetylmannose substituted sapphyrins. In these cases, the sugar unit was varied using the same protecting group.

Preparation of 8,17-di(tetrabenzoate-α,β-D-glucopyranoxypropyl)-3,12,13,22-tetraethyl-2,7,18,23-tetramethylsapphyrin, A21a. The same procedure as for tetraacetylderivative with α-D-glucopyranosylbromide tetrabenzoate (0.660 g, 1 mmol) gave product A21a in 97.6% yield. FAB MS m/e (rel. intensity):1817 (95, [MH]$^+$), 1818 (67, [MH$_2$]$^+$), 1816 (62, [M]$^+$). HRMS Calcd. for C$_{110}$H$_{105}$N$_5$O$_{20}$ 1815.7346. Found 1816.743117 ([MH]$^+$).

Preparation of 8,17 -di(α,β-D-glucopyranoxypropyl)3,12,13,22-tetraethyl-2,7,18,23-tetramethylsapphyrin, A21c. The product was prepared from protected derivatives (acetyl, benzoyl) by removal of the protecting group in methanol with a catalytic amount of sodium methoxide, or potassium hydroxide, or potassium cyanide. Pure product was obtained by crystallization, or reverse phase chromatography (C$_{18}$-modified silica gel) with methanol as a eluent. The yield of product A21c was 67%. FAB MS m/e (rel. intensity):986 (70, [M]$^+$), 987 (56, [MH]$^+$). HRMS Calcd. for C$_{54}$H$_{75}$N$_5$O$_{12}$ 985.54108. Found 985.5417. Elemental analysis: calc. 65.77% C, 7.67% H, 7.10% N; found 65.65% C, 7.69%H, 7.04%N. UV/VIS (H$_2$O): λ$_{max}$ 416,597.5, 642, 712; (MeOH): λ$_{max}$ 445.

EXAMPLE 3

Synthesis of Sapphyrin Bis(glycosamides)

Sapphyrin bis(glycosamides) were prepared by condensation of an activated form of the above-described sapphyrin acid (acid chloride, mixed anhydride, O-acylurea, N-acylimidazole derivative) with free, or O-acetylated glycoamines (2-amino-2-deoxy-glucopyranose, mannopyranose, galactopyranose).

Preparation of 3,12,13,22-Tetraethyl-8,17-bis[1,3,4,6-tetra-O-acetyl-2-amino-2-deoxy-α,β-D-glucopyranose)-carbonylethyl]-2,7,18,23-tetramethylsapphyrin A22a. Sapphyrin bis acid structure A19 (69 mg, 0.1 mmol) was converted to bis acid chloride as previously described. Bis acid chloride was dissolved in dry dichloromethane under argon and was slowly added to a solution of 1,3,4,6-tetra-O-acetyl-2-amino-2-desoxy-α-D-glucopyranose (0.1736, 0.5 mmol) in dichloromethane, which also contained 10 mg of 4-dimethylaminopyridine and 0.5 ml of dry pyridine at room temperature. The reaction mixture was stirred for 14 hours, then washed with water, the organic layer was evaporated and the product obtained by column chromatography on silica gel with dichloromethane containing 2–10% methanol as an eluent. The yield of product A22a was 114.6 mg (85.0%). $^1$H NMR spectrum (300 MHz, CDCl$_3$): δ=–4.91, –4.59, 1.94, 2.06, 2.12, 2.27, 3.41, 3.689, 3.84, 3.91, 3.93, 4.05, 4.12, 4.22, 4.54, 4.63, 4.72, 5.04, 5.19, 5.22, 11.59, 11.69. FAB MS, m/e (rel. intensity):1347 (96, [M]$^+$), 1348 (84, [MH]$^+$). HRMS: Calcd. C$_{70}$H$_{89}$N$_7$O$_{20}$ 1347.61428. Found 1347.61624.

Preparation of 3,12,13,22-Tetraethyl-8,17-bis[(2-amino-2-deoxy-α,β-D-glucopyranose)-carbonyethyl]-2,7,18,23-tetramethylsapphyrin, A22b. The above-described acetylated sapphyrin derivative A22a (13.4 mg, 0.01 mmol) was dissolved in methanol (10 ml) and a solution of 3 mg KOH in methanol was added. The reaction mixture was stirred for 4 hours and then the pH adjusted to 6 by adding hydrochloric acid. After evaporating to dryness, the product was crystallized from methanol-dichloromethane (1:1), or obtained by reverse phase chromatography with methanol as eluent. The yield of product A22b was 10.38 mg (88.0%). FAB MS, m/e (rel. intensity): 1012 (76, [MH]$^+$), 1011 (54, [M]$^+$). UV/VIS (H$_2$O): λ$_{max}$ 413,621,671.

Deacetylation could also be achieved under basic conditions by using, e.g., NH$_3$ in methanol, sodium methoxide in methanol, DABCO in methanol, or KCN in methanol, each with good yields.

EXAMPLE 4

Synthesis of Mono- and Bis-saccharide-Substituted Sapphyrins

In general, saccharide-substituted sapphyrins were prepared by the reaction of an activated sapphyrin mono- or bis-acid and a polyhydroxy-amino component.

Preparation of 3,8,17,22-tetraethyl-12-(carboxyethyl)-2, 7,13,18,23-pentamethylsapphyrin A23a. Part a: Preparation of 3,8,17,22-tetraethyl-12-(methoxycarbonylethyl)-2,7,13, 18,23-pentamethylsapphyrin. In accordance with the general optimized procedure for the production of substituted sapphyrins[4a], 4,4'-diethyl-5,5'-diformyl-3,3'-dimethyl-2,2'-bipyrrole (272 mg, 1.0 mmol) and 2,5-bis(5-carboxy-3-ethyl-4-methylpyrrol-2-ylmethyl)-3-methoxycarbonylethyl-4-methylpyrrole (523 mg, 1.0 mmol) were condensed to give sapphyrin A23a in 75.4% yield (0.490 g). $^1$H NMR (300 MHz, CDCl$_3$): δ–4.78 (1H, s, NH), –4.76 (1H, s, NH), –4.32 (1H, s, NH), –4.13 (2H, s, NH), 2.35–2.43 (12H, m, CH$_2$C$\underline{H}_3$), 3.85 (2H, t, CH$_2$C$\underline{H}_2$CO$_2$CH$_3$), 3.99 (3H, s, CH$_3$), 4.29 (6H, s, CH$_3$), 4.38 (3H, s, CH$_3$), 4.44 (3H, s, CH$_3$) 4.67–4.74 (8H, m, C$\underline{H}_2$CH$_3$), 5.22 (2H, t, C$\underline{H}_2$CH$_2$CO$_2$CH$_3$), 11.82 (1H, s, meso-H), 11.85 (1H, s meso-H), 11.88 (2H, s, meso-H). $^{13}$C NMR (75 MHz, CDCl$_3$): δ=12.7, 13.1, 15.9, 17.8, 17.9, 21.0, 23.0, 37.1, 52.1, 91.5, 92.0, 98.3, 98.4, 126.9, 127.0, 129.5, 129.6, 130.2, 132.7, 132.8, 134.7, 135.3, 135.5, 136.6, 136.7, 137.7, 139.1, 141.5, 141.7, 173.3. HRMS: Calcd. for C$_{41}$H$_{49}$N$_5$O$_2$: 643.3886. Found 643.3887.

Part b: preparation of sapphyrin acid A23a. A ca. 1:1 v.v. mixture of trifluoroacetic acid and conc. hydrochloric acid (10 ml for 100 mg of starting sapphyrin) was used to hydrolyze the ester. The reaction was run at 50° C. for 2 days after which time the desired sapphyrin acid product was obtained as its bis HCl adduct. After drying in vacuo, this protonated product was purified by column chromatography on silica gel (methanol 5% in dichloromethane, eluent). The yield was ca. 95%. $^1$H NMR (300 MHz, CDCl$_3$): δ=–5.84 (2H, bs, NH), –5.35 (3H, bs, NH), 2.20 (12H, t, C$\underline{H}_3$CH$_2$), 3.23 (2H, t, CH$_2$C$\underline{H}_2$CO$_2$H), 4.03 (3H, s, CH$_3$), 4.15 (6H, s, CH$_3$), 4.23 (3H, s, CH$_3$), 4.41 (3H, s, CH$_3$), 4.65 (4H, q, C$\underline{H}_2$CH$_3$), 4.74 (4H, q, C$\underline{H}_2$CH$_3$), 4.79 (2H, m, C$\underline{H}_2$CH$_2$CO$_2$H), 11.42 (2H, s, meso-H), 11.55 (1H, s, meso-H), 11.58 (1H, s, meso-H). $^{13}$C NMR (75 MHz, CDCl$_3$): δ=12.7, 12.9, 14.3, 15.9, 17.7, 17.9, 20.6, 20.9, 22.8, 36.5, 36.7, 61.9, 91.6, 98.1, 120.7, 120.9, 125.4, 125.4, 127.3, 129.1, 129.2, 130.0, 132.7, 132.8, 134.8, 134.9, 135.2, 135.4, 135.6, 135.7, 136.1, 136.8, 136.9, 137.0, 137.7, 139.31, 141.4, 141.8, 141.8, 174.4. FAB MS, m/e (rel intensity): 631 (48, [M+2H]$^+$), 630(100, [M+H]$^+$), 629 (52, M$^+$); HRMS: Calcd. for C$_{40}$H$_{47}$N$_5$O$_2$: 629.3730. Found 630.3798 [M+H]$^+$; for C$_{40}$H$_{48}$N$_5$O$_2$ [M+H]$^+$: calcd. 630.3808.

Reaction of the sapphyrin monoacid, 3,8,17,22-tetraethyl-12-(carboxyethyl)-2,7,13,18,23-pentamethylsapphyrin (A23a) with 2-deoxy-2-aminopyranosides: For these kinds of products, the above named sapphyrin monoacid was activated (via conversion to its acid chloride, a carbodiimide derivative, an NHS ester, or mixed anhydride) and reacted with the chosen amino-saccharide derivative (or a protected form thereof) to give the corresponding sapphyrin glycosamides.

3,8,17,22-Tetraethyl-12-[(2-amido-2-deoxy-α,β-D-galactopyranose)-ethyl]-2,7,13,18,23-pentamethylsapphyrin Ib. Sapphyrin monoacid A23a (3,8,17,22-tetraethyl-12-(carboxyethyl)-2,7,13,18,23-pentamethylsapphyrin) (63 mg, 0.1 mmol) was dissolved in 5 ml of dry DMF. Then, 1,1'-carbonyldiimidazole was added (32 mg, 0.2 mmol) and the reaction mixture stirred at room temperature for 2 hours. A solution of D-galactosamine-HCl in 3 ml of water containing 0.3 ml of pyridine was then slowly added. The resulting reaction mixture was stirred for 2 days before being worked up in accord with the following procedure: Sodium bicarbonate (5 ml of a saturated aqueous solution) was first added. Then after 5 min, the resulting precipitated product (A23b) was filtered off, washed with cold water (3 ml) and dried.

The same procedure as described above could also be used for the preparation of A23c–A23e when D-glucosamine.HCl, D-mannosamine.HCl and L-mannosamine-.HCl were used as alternative sugar moiety sources. Alternatively, substituted systems derived from 2-amino-2-deoxy-α-D-glucopyranose residue could be prepared via the use of 1,2,3,4-tetra-O-acetyl-2-amino-2-deoxy-α-D-glucopyranose hydrobromide (ref. S. Hanessian: Methods in Carbohydrate Chemistry, Vol. 6, 208) in the key coupling step. In addition, as another kind of variant, EDC, diisopropylcarbodiimide, or NHS ester activation could be employed to achieve the critical sapphyrin acid activation process. In all cases, the crude sapphyrin glucosamides were obtained in 65–75% yield and were purified via reverse column chromatography or via conversion (when necessary) to the corresponding 1,2,3,4-tetra-O-acetyl derivatives and purification as such. In these latter instances, acetylation was effected using acetic anhydride in pyridine and chromatography was carried out on silica gel using methanol 2% in dichloromethane as the eluent. Removal of the acetyl groups was then effected using either acid catalysis (trace of HCl) or basis hydrolysis (KOH in methanol for 6 hours).

Characterization data for the exemplary compound, 3,8,17,22-tetraethyl-12-[(2-amido-2-deoxy-α,β-D-galactopyranose)-ethyl]-2,7,13,18,23-pentamethylsapphyrin (A23b): FAB HRMS: Calcd for C$_{46}$H$_{59}$N$_6$O$_6$ ([M+H]$^+$): 791.449604; found: 791.457003. Anal.: Calcd. for C$_{46}$H$_{58}$N$_6$O$_6$ (791.01): 69.85% C, 7.39% H, 10.62% N; found. 69.60% C, 7.45% H, 10.49% N.

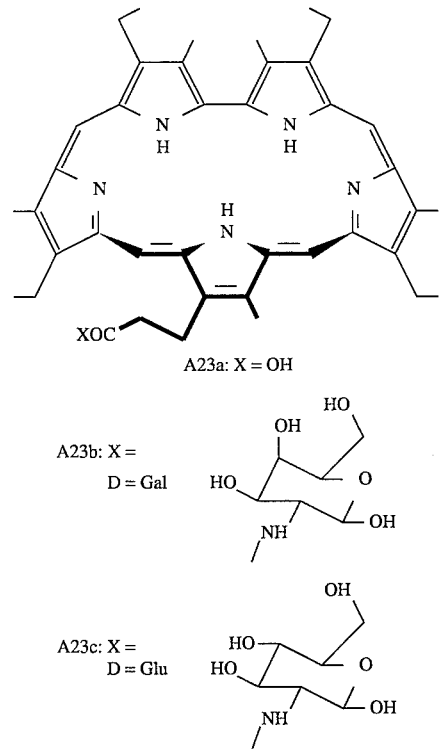

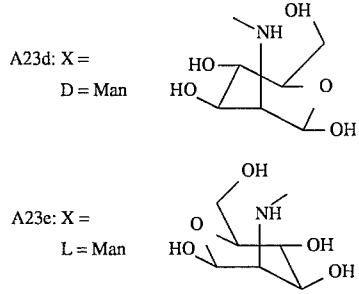

A23d: X =
D = Man

A23e: X =
L = Man

A strategy analogous to that given above (i.e., activation with 1.1 mol. eq. of a dehydrating reagent such as EDC, diisopropylcarbodiimide or 1,1'-carbonyl-diimidazole; and then coupling with 1.1 molar eq. of the aminocomponent) could also be used for the preparation of glycosamide derivatives of either the sapphyrin bisacid, 3,12,13,22-tetraethyl-8,17-bis(carboxyethyl)-2,7,18,23-tetramethylsapphyrin A19, or its monoester, monoacid analogue A24, 3,12,13,22-tetraethyl-8-(carboxyethyl)-17-(methoxycarbonylethyl)-2,7,18,23-tetramethylsapphyrin. In the latter case, deprotective removal of the methyl ester could be effected using a 1:1 mixture of HCl and TFA at 50° C. for 4 hours. This provides a precursor compound for sapphyrin-saccharide derivatives having structures A6, A7 and A26. Structure A7 with the sugar hydroxyls blocked with acetyls or other protecting R groups, provides a convenient starting material for the ligative coupling with an amine-containing component and, as a result of this, is extremely useful for the synthesis of unsymmetrical water soluble sapphyrins.

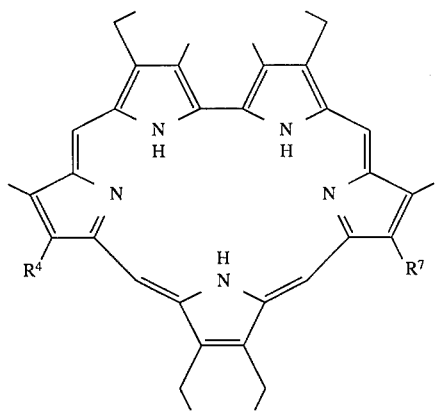

A19: R$^4$ = CH$_2$CH$_2$COOH, R$^7$ = CH$_2$CH$_2$COOH
A24: R$^4$ = CH$_2$CH$_2$COOH, R$^7$ = CH$_2$CH$_2$COOCH$_3$
A25: R$^4$ = CH$_2$COOH, R$^7$ = CH$_2$COOH

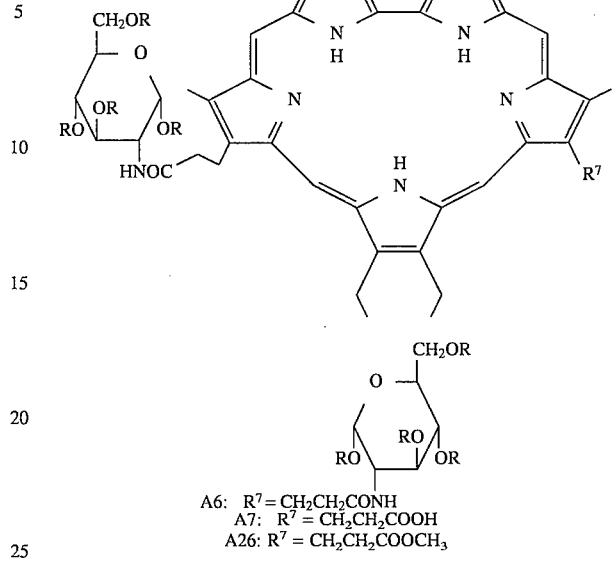

A6: R$^7$ = CH$_2$CH$_2$CONH
A7: R$^7$ = CH$_2$CH$_2$COOH
A26: R$^7$ = CH$_2$CH$_2$COOCH$_3$

The R groups on the saccharide moiety may be hydrogen, alkyl, aryl or acyl. Preferably, R is methyl, acetyl, benzyl, or trimethylsilyl.

EXAMPLE 5

Preparation of Sapphyrin Gluconamides

In general, the activated sapphyrin mono-(A23a) and bis acids (A19, A25) described in Example 4 were reacted with 1-amino-1-deoxy-D-sorbitol (or, in general, any D-glucamine in DMF-water (or aqueous buffer, pH 7.5–9) mixtures to give the sapphyrin gluconamides. Here, activation was effected using carbodiimide derivatives such as EDC or 1,3-diisopropylcarbodiimide or via the use of mixed anhydrides.

3,12,13,22-Tetraethyl-8,17-bis[(1-amido-1-deoxy-D-glucitol)ethyl]-2,7,18,23-tetramethylsapphyrin IVa. 3,12,13,22-tetraethyl-8,17-bis(carboxyethyl)-2,7,18,23-tetramethylsapphyrin A19 (Example 4) (69 mg, 0.1 mmol) was dissolved in dry DMF (5 ml) and cooled to 0° C. EDC (96 mg, 5 mmol) was then added together with 5 mg of 1-hydroxybenzotriazol. The resulting solution was stirred with external ice bath cooling for 1 hour. At this juncture, the chosen D-glucamine [in this case, 1-amino-1-deoxy-D-glucitol; alternative name: 1-amino-1-deoxysorbitol)] (108.7 mg, 6 mmol) in water (3 ml) and 4-dimethylaminopyridine (3 mg) were slowly added. Following this addition, the reaction mixture was stirred with cooling for 1 additional hour before being stirred for 3 more days at r.t. Work up consisted of adding 3 ml of saturated solution of sodium bicarbonate and then filtering off the resulting precipitate 5 minutes later. The resulting product A4 was washed with cool water (3 ml) and dried. Yield of A4 50.9 mg (60.81%). Characterization data: FAB HRMS: Calcd for $C_{54}H_{76}N_7O_{12}$ ([M+H]$^+$): 1014.555197; found 1014.557099. UV-vis $\lambda_{max}$: 424.5, 616, 681, 738 ($H_2O$, pH 2); 400.0, 421.5, 556, 623, 674 ($H_2O$, pH 7).

The same procedure was applied in the case of 3,12,13, 22-tetraethyl-8,17-bis(carboxymethyl)-2,7,18,23-tetramethylsapphyrin A25 (Example 4). The resulting product A5, was obtained in 69.5% yield.

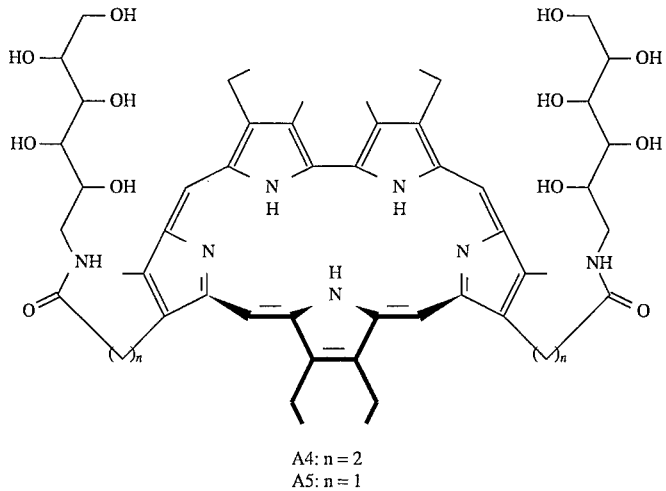

A4: n = 2
A5: n = 1

EXAMPLE 6

Preparation of Polysaccharide Substituted Sapphyrins

Sapphyrin Substituted by a Low Molecular Weight Chitosan. In this study, chitosan

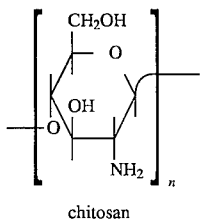

chitosan (poly(1,4-β-D-glucopyranosamine; alternative name: 2-amino-2-deoxy-(1–4)-β-D-glucopyranan, Fluka, Ronkonkoma, N.Y.; $M_r$~70,000, n is from about 200 to 500, preferably about 350) was used for coupling and was attached to the activated form of the sapphyrin monoacid A23a (i.e., 3,8,17,22-tetraethyl-12-(carboxyethyl)-2,7,13, 18,23-pentamethylsapphyrin) via an amide bond. Specifically, the sapphyrin monoacid (31.5 mg, 0.05 mmol) was dissolved in dry DMF (3 ml). After cooling with an external ice bath, EDC (50 mg) was added. The resulting activation process was allowed to proceed for 1 hour. At this juncture, a saturated solution of chitosan in TEAB (triethylammonium hydrogen carbonate) buffer, pH 8.5 (3 ml) was added. The reaction mixture was held for another 1 hour in the external ice bath. It was stirred for additional 7 days at r.t., then subjected to 1 hour of stirring in an ultrasonic bath. The final, resulting reaction mixture was evaporated in vacuo, redissolved in water (5 ml), filtered, and evaporated to dryness.

This water-soluble product A23f was characterized by studying its interactions with DNA in a PIPES buffer at pH 7. Here, for instance, it was found that the sapphyrin substituted chitosan gave a detectable CD spectrum only after the addition of DNA.

A Sapphyrin Substituted Alginic Acid. In this study, alginic acid (a mixed polymer of mannuronic and glucuronic acid, $M_r$~48,000–186,000, n is from about 100 to about 500, preferably 300, Fluka, Ronkonkoma, N.Y.) and 3,8,17,22-tetraethyl-12-[(2-aminoethyl)-aminocarbonylethyl]-2,7,13, 18,23-pentamethylsapphyrin A27d were used as the coupling partners with the key linkage being established again via an amide bond. Specifically, a saturated solution of alginic acid in a 5 ml water-pyridine mixture (4:1) was prepared using an ultrasonic bath. The resulting solution was cooled using an external ice bath before EDC (50 mg) was added. This activation reaction was kept cool for 1 hour before a solution of sapphyrin A27d (10 mg) in DMF (3ml) was added. The resulting reaction mixture was first stirred with external ice bath cooling for 1 hour and then for 7 days at r.t. and then, finally, for 1 hour in an ultrasonic bath. Following this, the solvents were removed by evaporation in vacuo. The resulting residues were redissolved in water, filtered, and then retaken to dryness in vacuo. In this case, the product demonstrated a CD spectrum (PIPES buffer, pH 7) that was not substantially changed upon the addition of DNA.

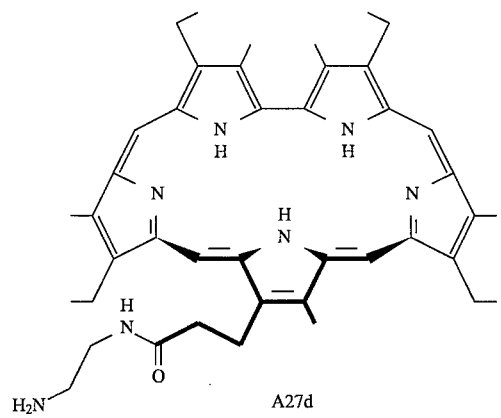

A27d

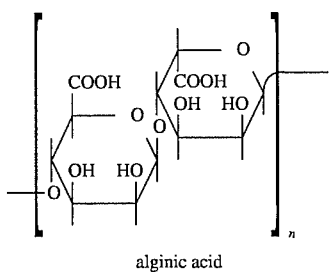

alginic acid

By use of the above procedure, or modest modifications thereof known to one of skill in the art in light of this disclosure, it is possible to prepare sapphyrin substituted hyaluronic acid derivatives A27b (for the needed precursor, see: *J. Am. Chem. Soc.* 1994, 116, 7515–7522) or dextran substituted sapphyrins A27c (for the needed precursor, see: *Arch. Biochem. Biophys.* 1975, 169, 464–473).

EXAMPLE 7

Sapphyrin-DNA Interactions

The present inventors have discovered that sapphyrin binds to double- and single-stranded DNA and RNA, and furthermore, that it does so in a novel and unexpected manner.

Sapphyrin Binds to DNA: The first evidence for sapphyrin DNA binding came from the observation that an excess of sapphyrin, which is green in solution, can rapidly and specifically precipitate green DNA fibers. The inventors propose that this binding and precipitation is due to the chelation of the polyanionic sugar phosphate backbone of DNA by sapphyrin. This leads to charge neutralization and through the resulting hydrophobic effects, the DNA falls out of solution. Such precipitation effects have not been reported for other DNA binding compounds which are known to either intercalate or groove bind with DNA.

Further evidence that sapphyrin binds to DNA was provided by CD spectroscopy, a technique that can detect chirality. Sapphyrin is an achiral macrocycle that shows no significant CD spectra by itself in solution. However, in the presence of DNA, a sapphyrin CD spectrum was induced. This is consistent with relatively rigid binding to DNA, a chiral macromolecule, which places sapphyrin in a chiral environment and yields the observed induced CD effect.

In addition, UV-visible spectroscopy provides still further evidence that sapphyrin binds DNA. Upon addition of a large excess of DNA, changes in the visible absorption spectrum occur. The Soret-like transition that occurs at 410 nm is red-shifted by approximately 12 nm. This is taken as evidence that DNA is interacting directly with the sapphyrin macrocycle.

Finally, the inventors have determined that sapphyrin exhibits enhanced fluorescence in the presence of DNA. Sapphyrin alone shows only minimal fluorescence in aqueous buffered solution, but has been shown to either dimerize or aggregate in polar solvents resulting in a quenching of the sapphyrin fluorescence. The fluorescence enhancement effect discovered by the inventors is thus considered to be the result of binding to DNA which breaks up the dimers/aggregates and creates "monomeric" sapphyrins bound to DNA. Using this fluorescence enhancement as measurement of binding, the lower limit of the apparent binding constant has been estimated to be approximately $10^6$ $M^{-1}$.

Sapphyrin-DNA Binding is not Intercalation or Groove Binding: Unwinding of double helical DNA has traditionally been accepted as a signature of DNA intercalators. Based on the apparent binding constant obtained using fluorescence spectroscopy, the inventors conducted topoisomerase-based unwinding studies using concentrations of sapphyrin where the sapphyrin macrocycle was significantly bound to the DNA. In such studies, no sapphyrin-mediated DNA unwinding was detected, leading to the conclusion that sapphyrin cannot be intercalating.

Preliminary results have indicated that nearly identical visible absorption changes can be observed when sapphyrin is titrated with either double-stranded DNA or single-stranded DNA. As single-stranded DNA contains no higher order structure, such as a major or minor groove, and the interaction appears to be spectroscopically identical between the two types of DNA, this data demonstrates that sapphyrin cannot be groove binding.

Sapphyrin Binds to the Phosphate Backbone of DNA: Recent X-ray crystallographic evidence has shown that the sapphyrin macrocycle can bind both monobasic phosphoric acid and monobasic phenyl phosphate 13. The inventors conducted a study aimed to link this solid state evidence to the interaction between sapphyrin and DNA which occurs in solution. They found that, in solution, spectroscopic similarities exist between sapphyrin in the presence of DNA and sapphyrin in the presence of diethyl phosphate. The latter is a simple phosphate that compares with the phosphates used in the X-ray crystallographic studies.

UV-visible spectral shifts comparable to those obtained with DNA can be observed when sapphyrin is titrated with diethyl phosphate. With diethyl phosphate, the Soret-like transition is red-shifted by approximately 9 nm. In addition, fluorescence enhancement in the presence of diethyl phosphate can be observed as in the case with DNA. The only structural similarity between this simple phosphate and the DNA is the phosphate anion and, when taken in conjunction with the X-ray crystallographic data, these spectroscopic techniques provide evidence for the novel mode of DNA binding proposed by the present inventors.

Porphyrins and Sapphyrins Interact Differently with DNA: To demonstrate that sapphyrins interact differently with DNA than their nearest relatives, porphyrins, the inventors synthesized a porphyrin which was functionalized in a similar manner as the sapphyrin A1. Spectroscopically, these two molecules act very differently in the presence of DNA. Neither an induced CD effect nor any significant shifts in the visible absorption spectrum are observed with the functionalized porphyrin in the presence of DNA. In contrast to the fluorescence enhancement of sapphyrin, the porphyrin shows a decrease in fluorescence intensity in the presence of DNA.

The novel findings described in this example form the basis for even further uses of sapphyrin and sapphyrin derivatives as tools in the research or clinical laboratory. A particularly important application contemplated by the present inventors is to use sapphyrin, or derivatives thereof, in recovering DNA samples, for example, after electrophoresis. This may be applied as a general technique, or adapted for more specific DNA recognition and recovery by employing functionally derivatized sapphyrins having nucleobase specificity.

EXAMPLE 8

Photocleavage of pBR322 Plasmid DNA in the Presence of Sapphyrin

Photocleavage of DNA with water-soluble tetrahydroxysapphyrin A1 was monitored using pBR322 plasmid.

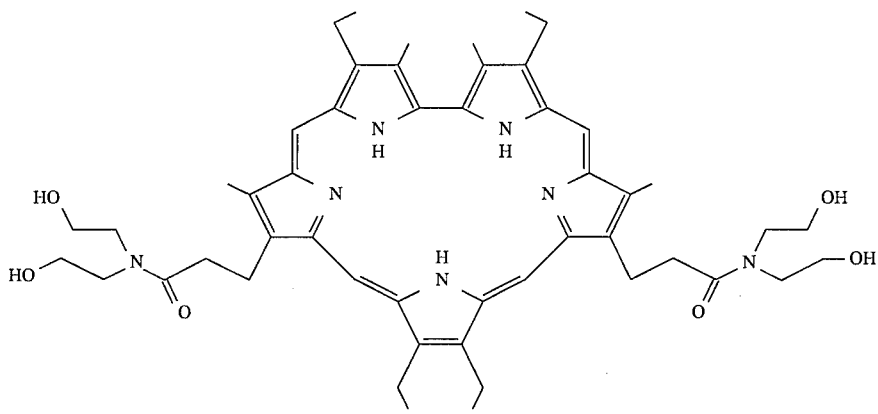

A1

The irradiated solutions consisted of 100 μL of 0.1 SSC buffer (saline sodium citrate: 15 mM NaCl, 1.5 mM sodium citrate, pH 7.0) containing 32 μM pBR322 DNA phosphates and either 0 or 4 μM sapphyrin. Plasmid pBR322 was purchased from Gibco BRL and contained ≧90% of the material as Form I, i.e., supercoiled DNA. The solutions were irradiated at room temperature with a high pressure Xenon lamp through a pyrex filter to stop UV light of wavelengths below about 300 nM. The samples were irradiated in a quartz cuvette measuring 1 mm in diameter and received approximately 3400 W/m². After irradiation, 3 μL 50% glycerol/water loading buffer containing bromophenol blue was added to 9 μL irradiated solution. The samples were analyzed on an 0.8% agarose gel containing ethidium bromide in Tris-acetate buffer at 90 V for 30 minutes. The DNA was detected by fluorescence using a UV lamp.

Analysis of two control lanes, one in the absence of sapphyrin and one in the presence of sapphyrin with no light exposure, indicated that >90% of the plasmid DNA was Form I DNA, i.e., supercoiled DNA. Analysis of the three experimental lanes where sapphyrin was incubated with the DNA with light exposure for 10, 20 and 40 minutes indicated that incubation with sapphyrin at 4 μM concentration caused photocleavage of Form I DNA to Form II and III DNA, i.e., supercoiled DNA was cleaved to form nicked DNA having one single strand break and linear DNA having a double-strand break. At 40 minutes of light exposure, >90% of the plasmid DNA was either Form II (nicked) or Form III (linear) DNA.

These data demonstrate the utility of the herein-described sapphyrins for photoinduced cleavage of DNA and for use as a photodynamic agent. The ability to further modify sapphyrin molecules via appended functional groups and thereby fine-tune receptor specificity and localization provides an advantage of the water-soluble sapphyrins over those that are exclusively alkyl substituted.

EXAMPLE 9

Water-Soluble Sapphyrins as Therapeutic Agents

The discoveries embodied by the present invention may be advantageously exploited in further scientific research, and importantly, in the development of new methods and compositions for treating various human diseases including cancer. The sapphyrin-saccharide derivatives are envisioned to be of use in a wide variety of clinical embodiments, especially due to specific cellular targeting from saccharide recognition by specific receptors. Sapphyrins and modified sapphyrins also have potential for use directly as chemotherapeutics.

Sapphyrin may also be used as a delivery agent for the intracellular targeting of any drug that has a phosphate group. Of course, given the synthetic methodology disclosed herein, it is contemplated that the sapphyrin may be derivatized by the introduction of further groups to the periphery of the macrocycle, which groups would add the specificity and/or selectivity of the sapphyrin-drug interaction. Sapphyrin-drug interactions of this sort may be based upon either non-covalent interactions, or alternatively, may employ a covalent bond that is cleaved on exposure to the intracellular environment.

The newly-discovered interaction between sapphyrin and DNA, in which sapphyrin acts as a chelate for the phosphate backbone of DNA, is particularly important. The binding constant of unmodified sapphyrin for DNA has been determined to be on the order of $10^6$ $M^{-1}$ and evidence shows that the mode of DNA binding is not intercalation or groove binding. The inventors will extend these findings and construct, using all the available experimental evidence, computer models of the sapphyrin-DNA interaction. These models will allow the design and engineering of covalently linked multimeric sapphyrin molecules with increased affinity and specificity.

These second-generation multimeric sapphyrin-based constructs should have a DNA affinity high enough to interfere with biological processes such as transcription and translation. It is contemplated that this will ultimately lead to the development of sapphyrin-based therapeutic agents for use in treating a variety of human diseases, including cancer.

Sapphyrin molecules themselves are also contemplated for use directly as chemotherapeutic agents. Currently available chemotherapeutics generally have complex structures, or complicated modes of interaction with their targets, that preclude systematic improvement. The development of a novel class of DNA binding compounds, namely the sapphyrins of the present invention, therefore provides important new opportunities for the development and use of novel therapeutic agents.

Due to the unique mode of sapphyrin-DNA interaction, the sapphyrin molecule possesses an unrivaled ability to act as a general DNA binding platform. Binding can also be modified so as to adjust both target cell specificity and degree of interaction with the DNA. For sapphyrins, importantly, the basic site of interaction with the DNA involves the interior of the sapphyrin macrocycle, so that the exterior positions $R^1$–$R^{10}$ can be substantially modified without significantly disrupting the DNA binding interaction. These exterior positions can be used to systematically adjust features such as solubility, membrane permeability and cell selectivity. Furthermore, groups designed to modulate interaction with DNA can be attached to the exterior of the sapphyrins including alkylating functions (bromoacetamido groups, epoxides etc.) to provide covalent attachment to DNA or ene-diyne moieties to allow for double stranded DNA cleavage.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. For example, other macrocyclic, positively-charged entities can be envisioned as binding to phosphate-containing species such as nucleotides, oligonucleotides and DNA by means of the same or similar oriented electrostatic interactions described herein. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.
1. Sessler, J. L. and Burrel, A. K., *Topics in Current Chemistry*, 1991, 161, 177–273.
2. V. J. Bauer et al., *J. Am. Chem. Soc.* 105 1983 6429–6436.
3. M. J. Broadhurst et al., *J. Chem. Soc., Perkin Trans.* 1 1972, 2111–2116.
4. (a) J. L. Sessler et al., *J. Am. Chem. Soc.*, 112 1990 2810–2813. (b) M. Shionoya et al., *J. Am. Chem. Soc.* 114 1992, 5714–5722.
5. H. Furuta et al., *J. Am. Chem. Soc.* 113 1991 6677–6678.
6. J. L. Sessler et al., *Synlett.* 1991 127–133.
7. A. K. Burrell et al., *Angew. Chem.* 103 1991 83–85; Angew. Chem. Int. Ed. Engl. 30 (1991) 91–93.
8. J. L. Sessler et al., *J. Chem. Soc., Chem. Commun.* 1991, 1733–1735.
9. Cell Surface Carbohydrate Chemistry, Ed. R. E. Harmon, Academic Press, NY, 1978, p. 225, G. A. Jarnieson: Surface Glycopropteins of Normal and Abnormal Platelets p. 311: B. Paul, W. Korytnyk: Cell Surface as a target for chemotherapy. Potential inhibitors of Biosynthesis of Protein-Carbohydrate Linkage in Glycoproteins.
10. R. J. Bernacki et al., *J. Supramol. Structure.* 7, 235–250 1977.
11. R. R. Schmidt, W. Kinzy: *Adv. Carbohydrate Chem.*, 1994, 50, 21–119.
12. B. Verlhac, A. Gaudemer, I. Kraljic *New J. Chem.* 1984, 8, 401–406.
13. B. Iverson, K. Shreder, V. Kral, J. L. Sessler, *J. Am. Chem. Soc.* 1993, 115, 11022–11023.

What is claimed is:
1. A water-soluble sapphyrin having structure II:

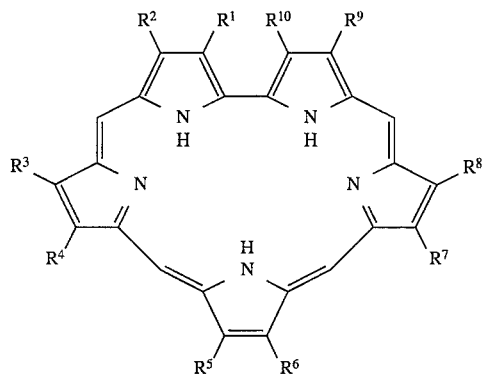

wherein each of $R^1$–$R^{10}$ are independently hydrogen, alkyl, alkene, alkyne, halide, alkylhalide, hydroxyalkyl, hydroxyalkylamido, glycol, polyglycol, thiol, thioalkyl, aminoalkyl, carboxyalkyl, carboxyamidealkyl, oxyalkyl, alkoxyalkyl, aryloxyalkyl, oxyhydroxyalkyl, alkyloxycarbonyl, aryloxycarbonyl, aldehyde, ether, ketone, carboxylic acid, phosphate, phosphonate, sulfate, phosphate substituted alkyl, phosphonate substituted alkyl, or sulfate substituted alkyl, such that the total number of carbon atoms in each substituent R is less than or equal to 100;

wherein at least one of $R^1$–$R^{10}$ is of the formula $(CH_2)_n$—A—$(CH_2)_m$—B, where A is alkyl having from 1–4 carbon atoms, oxy, sulfide, amide, carbonyl, alkenyl, alkynyl, alkylhalide, hydroxyalkyl, glycol, polyglycol, alkylthiol, substituted alkyl, phosphate, phosphonate, sulfate, phosphate substituted alkyl, phosphonate substituted alkyl, sulfate substituted alkyl, carboxy, carboxyamide, ester, thiol-substituted carboxyamide, or derivatized carboxyamide;

B is hydroxy, hydroxyalkyl, oxyalkyl, carboxy, carboxyalkyl, glycol, polyglycol, thiol, aminoalkyl, phosphate, phosphonate, sulfate, phosphate substituted alkyl, phosphonate substituted alkyl, sulfate substituted alkyl, substituted hydroxyalkyl, saccharide, saccharide derivative, or polysaccharide; and n and m are independently an integer from 0 to 4.

2. The water-soluble sapphyrin of claim 1, wherein

A is alkyl having 1–4 carbon atoms, oxy, sulfide, amide, carbonyl, carboxy, carboxyamide, ester, thiol-substituted carboxyamide, or derivatized carboxyamide; and B is hydroxy, hydroxyalkyl, saccharide, saccharide derivative or polysaccharide.

3. The water-soluble sapphyrin of claim 1, wherein B is hydroxyalkyl.

4. The water-soluble sapphyrin of claim 3 wherein the hydroxyalkyl is hydroxymethyl, hydroxyethyl, hydroxypropyl, or hydroxybutyl.

5. The water-soluble sapphyrin of claim 1 wherein A is carboxyamide and B is hydroxyalkyl.

6. The water-soluble sapphyrin of claim 1 wherein A is oxy and B is oxyalkyl.

7. The water-soluble sapphyrin of claim 1 wherein A is alkenyl and B is hydroxy.

8. The water-soluble sapphyrin of claim 1 wherein A is carboxyamide and B is saccharide.

9. The water-soluble sapphyrin of claim 1, further defined as having substituents $R^2$, $R^4$–$R^7$ and $R^9$ as set forth in Table 2 or 3.

10. The water-soluble sapphyrin of claim 2, where B is saccharide or saccharide derivative.

11. The water-soluble sapphyrin of claim 10, wherein the saccharide or saccharide derivative is selected from those set forth in Table 1.

12. The water-soluble sapphyrin of claim 1, where B is a polysaccharide.

13. The water-soluble sapphyrin of claim 12, where the polysaccharide is chitosan, alginic acid, hyaluronic acid or dextran.

14. The water-soluble sapphyrin of claim 1, wherein $R^5$ is of the formula $(CH_2)_n$—A—$(CH_2)_m$—B, where B is hydroxyalkyl or saccharide.

15. The water-soluble sapphyrin of claim 14 wherein B is saccharide and the saccharide is D-glucose, D-mannose, L-mannose, or D-galactose.

16. The water-soluble sapphyrin of claim 1, wherein $R^4$ is of the formula $(CH_2)_n$—A—$(CH_2)_m$—B, where B is hydroxyalkyl or saccharide.

17. The water-soluble sapphyrin of claim 1, wherein $R^7$ is of the formula $(CH_2)_n$—A—$(CH_2)_m$—B, where B is hydroxyalkyl or saccharide.

18. The water-soluble sapphyrin of claim 1, wherein $R^5$ is of the formula $(CH_2)_n$—A—$(CH_2)_m$—B, where B is carboxyalkyl.

19. The water-soluble sapphyrin of claim 1, wherein $R^7$ is of the formula $(CH_2)_n$—A—$(CH_2)_m$—B, where B is carboxyalkyl.

20. A water-soluble sapphyrin selected from sapphyrins A1–A27 of Table 2 or B1–B8 of Table 3.

* * * * *